United States Patent [19]
Szuhaj et al.

[11] 3,962,292

[45] June 8, 1976

[54] PHOSPHATIDE PREPARATION PROCESS

[75] Inventors: Bernard F. Szuhaj, Lombard; Joseph R. Yaste, Hoffman Estates, both of Ill.

[73] Assignee: Central Soya Company, Inc., Fort Wayne, Ind.

[22] Filed: July 29, 1974

[21] Appl. No.: 492,762

[52] U.S. Cl. .............................................. 260/403
[51] Int. Cl.$^2$ .......................................... C07F 9/10
[58] Field of Search ................................... 260/403

[56] References Cited
UNITED STATES PATENTS

| | | | |
|---|---|---|---|
| 2,445,948 | 7/1948 | Wittcoff | 260/403 |
| 2,629,662 | 2/1953 | Julian et al. | 260/403 X |
| 2,791,594 | 5/1957 | Hennessy et al. | 260/403 |
| 3,301,881 | 1/1967 | Davis | 260/403 |

*Primary Examiner*—Patrick P. Garvin
*Attorney, Agent, or Firm*—Dawson, Tilton, Fallon & Lungmus

[57] ABSTRACT

A procedure for modifying a natural phosphatide to develop water dispersability which includes steps of acylation, hydroxylation, and neutralization.

1 Claim, No Drawings

PHOSPHATIDE PREPARATION PROCESS

BACKGROUND AND SUMMARY OF INVENTION

Although the individual steps of acylation and hydroxylation of phosphatides are known (see U.S. Pat. Nos. 3,301,881 and 2,629,662, respectively), neither provides a product having desirable water dispersability characteristics. It was therefore surprising to discover that employing both steps in combination would result in a phosphatide having significantly improved water dispersability.

More particularly, it was surprising to discover that phosphatides (commonly referred to as "lecithins") can have substantially enhanced water dispersability characteristics when made more lipophilic by the addition of acyl groups according to the procedure of U.S. Pat. No. 3,301,881 and more hydrophilic by the addition of hydroxyl groups according to the process of U.S. Pat. No. 2,629,662.

In a preferred embodiment of the invention, we acylate the amino groups of a phosphatidic material utilizing a carboxylic acid anhydride containing not more than ten carbon atoms exclusive of any aryl groups and while the mixture is still at an acidic pH, hydroxylating the phosphatidic material with hydrogen peroxide, and thereafter substantially neutralizing the mixture.

DETAILED DESCRIPTION OF THE INVENTION

It is believed that the practice of the invention will be more readily understood from a consideration of the following examples:

EXAMPLE I

In this example, 400 grams of crude lecithin were weighed into a three-neck, three-liter flask fitted with a crescent stirrer and thermometer. The lecithin was commercially available from the Chemurgy Division of Central Soya Company, Inc., formerly the Chemurgy Division of the Glidden Company (at the time of U.S. Pat. No. 2,629,662). This lecithin at an acetone insolubles percent of 72, a free amino nitrogen content of 2.38 mg./g. and an iodine value of 101.2.

The lecithin was heated on a steam bath to 170°F and 12 grams (3% by weight) of acetic acid anhydride added and reacted for 30 minutes at 170°F with stirring.

Next, 40 grams (10% by weight) of 35% concentration hydrogen peroxide was added and reacted at 170°F for 1 hour with stirring.

Next, sodium hydroxide solution (50% concentration) was added to neutralize the product (8.8 grams or 2.2% being required) and mixed for 10 minutes and the product vacuum dried to 185°–190°F and about 28 inches vacuum. The hot product was then vacuum steam deodorized by the dropwise addition of 20% water and re-dried.

The product was then analyzed for free amino nitrogen according to the Formol titration procedure (see Patent 3,301,881) with the determination that the product had 0.38 mg./g. free amino nitrogen or a percentage reduction of 84%. The product was also analyzed for iodine value according to procedure Tg 1-64 of the American Oil Chemists Society. The iodine value of the product was 85.3 representing a percentage reduction of 15.7%. The resultant AI (acetone insolubles) value was 66%.

Next, a portion of the product was diluted to 60% AI with degummed soybean oil and subjected to the functionality test.

The functionality test to determine hydration and dispersability characteristics was as follows. Into 150 mls. of tapwater (8–9 grains hardness) in a 250 ml. beaker was vigorously stirred 3–4 grams of the lecithin produced by this example. The stirring was done with a small spatula for 60 seconds and the time was noted for the lecithin to form flocculant strings, a sign of hydration. Ordinarily, an arbitrary numerical rating was assigned as follows:

Hydration in 0–15 seconds Rating 4
Hydration in 16–30 seconds Rating 3
Hydration in 31–45 seconds Rating 2
Hydration in 46–60 seconds Rating 1
No hydration after 60 seconds Rating 0

The modified phosphatide of this example not only hydrated within 15 seconds (Rating 4) but was readily dispersed to form a milky white dispersion throughout the water.

In contrast to this, the commercial product made according to the acylation U.S. Pat. No. 3,301,881 (marketed as CA Lecithin) received a zero rating. Further, the commercial product of the hydroxylation U.S. Pat. No. 2,629,662 (marketed as Centrolene S) although hydrating at a rating of 4, did not exhibit any dispersability characteristics — the flocculant strings merely turning white, indicative of hydration, but remaining undispersed.

EXAMPLE II

In this example, ten different runs were made with varying concentrations of acetic anhydride and hydrogen peroxide to determine the effect thereof on dispersability. The acetic anhydride concentrations were 1, 2, 3 and 5% (based upon the dry weight of the lecithin) while the hydrogen peroxide concentrations were 1, 5 and 10% (again, based on the dry weight of the lecithin). In some instances 0.5% benzoyl peroxide was added but this seemed to be of insignificant effect. The procedure of Example I was followed in the case of each sample, i.e., acylation, hydroxylation and neutralization — in order. Here it should be noted that according to the preferred practice of the invention, we utilize the acidic pH remaining from the acylation reaction to develop the per acid resulting from the addition of hydrogen peroxide, the acid in this example being per acetic acid. In most cases both hydration and dispersability of the nature of that discussed in Example I resulted. It was only in those instances where either or both of the free amino nitrogen value and iodine value were at low levels of reduction that the hydration and dispersability of the nature of that discussed in Example I did not result. For example, the decrease in amino nitrogen is an indication of the degree to which the product had been acylated. According to U.S. Pat. No. 3,301,881, a suitable free-flowing lecithin is obtained when the percentage reduction of the order of at least 30% is achieved. Correspondingly, the iodine value is an indication of the degree of hydroxylation which reduces the number of double bonds in the product. According to U.S. Pat. No. 2,629,662 the minimum decrease in iodine value should be at least 5% with an economically feasible upper limit of about 20–25%. We found that to achieve both hydration and dispersability it was necessary to develop a relatively higher value in one step when a relatively lower value (iodine value or free amino acid value, as the case may be) results from the other step.

For example, requisite hydration and dispersability are achieved even with iodine value reductions of the order of 5–10% when the reduction in free amino nitrogen value is of the order of 60–70%. However, with iodine value reductions of the order of 3–4%, the desired dispersability could not be obtained with free amino acid reductions of the order of 30–60%.

EXAMPLE III

Here a series of laboratory runs were made according to the procedure of Example I but with the substitution of various other acid anhydrides for the acetic anhydride. Used for this example were the anhydrides of the following acids: maleic, succinic, phthalic, valeric and benzoic. In each case the concentration was based on a mol ratio equivalent to the 3% acetic anhydride and 10% hydrogen peroxide utilized for hydroxylation. In all cases, the desired dispersability was achieved, even with very low percentage reductions in free amino nitrogen. For example, the percentage reduction in the run utilizing phthalic anhydride was 10% and that with maleic anhydride was 18%. However, in each of those instances, the percentage reduction of the iodine value was at the upper end of the range, i.e., of the order of 20%.

While in the foregoing specification a detailed description of embodiments of the invention have been set down for the sake of illustration (and here express reference is made to U.S. Pat. Nos. 2,629,662 and 3,301,881 for additional details not herein given), many variations in the details may be made by those skilled in the art without departing from the spirit and scope of the invention.

We claim:
1. In a method of modifying a natural phosphatide to develop water dispersability, the steps of:
   acylating a vegetable material consisting predominantly of phosphatidic material by mixing said material with a carboxylic acid anhydride containing not more than ten carbon atoms exclusive of any aryl groups and continuing the reaction between said material and anhydride until the free amino nitrogen value of said material is reduced at least about 10% to about 90%,
   thereafter hydroxylating the acylated product while the mixture is still at an acid pH from said acylating step and continuing the reaction between said acylated product and the hydroxylating agent until the iodine value of said acylated product is reduced at least about 5% to about 20%,
   controlling the acylating and hydroxylating steps to develop a relatively higher reduction in one value when a relatively lower reduction in value results from the other step, and
   thereafter substantially neutralizing the acylated, hydroxylated product.

\* \* \* \* \*